United States Patent [19]
Lee et al.

[11] Patent Number: 5,654,189
[45] Date of Patent: *Aug. 5, 1997

[54] PREPARATION OF PURE CULTURES OF POST-MITOTIC HUMAN NEURONS

[75] Inventors: Virginia Lee; Samuel Pleasure, both of Philadelphia, Pa.

[73] Assignee: Trustees of the University of Pennsylvania, Philadelphia, Pa.

[*] Notice: The term of this patent shall not extend beyond the expiration date of Pat. No. 5,175,103.

[21] Appl. No.: 660,723

[22] Filed: Jun. 10, 1996

Related U.S. Application Data

[63] Continuation of Ser. No. 279,268, Jul. 22, 1994, abandoned, which is a continuation of Ser. No. 170,668, Dec. 17, 1993, abandoned, which is a continuation of Ser. No. 911,980, Jul. 10, 1992, abandoned, which is a division of Ser. No. 780,715, Oct. 21, 1991, Pat. No. 5,175,103.

[51] Int. Cl.$^6$ .............................. C12N 5/06; C12N 5/10
[52] U.S. Cl. ................................................ 435/368
[58] Field of Search ...................... 435/240.2, 240.21, 435/172.3, 320.1

[56] References Cited

U.S. PATENT DOCUMENTS

| | | | |
|---|---|---|---|
| 4,829,000 | 5/1989 | Kleinman et al. | 435/240.23 |
| 5,032,407 | 7/1991 | Wagner et al. | 424/520 |
| 5,171,678 | 12/1992 | Behr et al. | 435/172.3 |
| 5,175,103 | 12/1992 | Lee et al. | 435/172.3 |
| 5,180,820 | 1/1993 | Barde et al. | 536/23.51 |
| 5,270,191 | 12/1993 | McKay et al. | 435/172.3 |

OTHER PUBLICATIONS

Schubert, et al., "Neuronal Cells from Rodent Neoplasms" 1979 Cell Culture: Methods of Enzymology, Eds. Jakoby, WB and IH Pastan, pp. 584–590.

Andrews et al., "Pluripotent Embryonal Carcinoma Clones Derived from the Human Teratocarcinoma Cell Line Tera-2," *Lab. Invest.* 50:147–162, 1984.

Andrews, Peter W., "Retinoic Acid Induces Neuronal Differentiation of a Cloned Human Embryonal Carcinoma Cell Line in Vitro," *Developmental Biology* 103:285–293, 1984.

Bartlett et al., "Immortalization of mouse neural precursor cells by the c-myc oncogene," *Proc. Natl. Acad. Sci. USA* 85:3255–3259, 1988.

Birren et al., "A v-myc-Immortalized Sympathoadrenal Progenitor Cell Line in Which Neuronal Differentiation Is Inhibited by FGF but Not NGF," *Neuron* 4:189–201, 1990.

Carden et al., "Two-Stage Expression of Neurofilament Polypeptides During Rat Neurogenesis with Early Establishment of Adult Phosphorylation Patterns," *J. Neurosci.*, 7:3489–3504, 1987.

Cepko, Constance L., "Immortalization of Neural Cells Via Retrovirus-Mediated Oncogene Transduction," *Ann. Rev. Neuro.*, 12:47–65, 1989.

Chiu et al., "Characterization of a Novel 66 kd Subunit of Mammalian Neurofilaments," *Neuron*, 2:1435–1445, 1989.

Dubois et al., "Monoclonal Antibody A2B5, Which Detects Cell Surface Antigens, Binds to Ganglioside $G_T^3$ ($II^3$ (NeuAc)$_3$LacCer) and to Its 9–0–Acetylated Derivative," *J. Biol. Chem.*, 265:2797–2803, 1990.

Fredericksen et al., "Immortalization of Precursor Cells from the Mammalian CNS," *Neuron* 1:439–448, 1988.

Geisert et al., "Expression of microtubule-associated protein 2 by reactive astrocytes," *Proc. Natl. Acad. Sci. USA*, 87:3967–3971, 1990.

Geller et al., "'A Defective HSV-1 Vector Expresses *Escherichia coli* β–Galactosidase in Cultured Peripheral Neurons," *Science*, 241:1667–1669, 1988.

Goslin et al., "Changes in the Distribution of GAP-43 During the Development of Neuronal Polarity," *J. Neurosci.*, 10:588–602, 1990.

Greene and Tischler, *Advances in Cellular Neurobiology*, S. Federoff and L. Hertz, eds., New York: Academic Press, 1982. pp. 380–391.

Gupta et al., "Effects of antimitotic drugs on the morphological features of PC12 cells in culture–a light and EM Study," *Chem. Abstracts*, 107:29, Abstract No. 51507, 1987.

Gupta et al., "Effects of Antimitotic Drugs on the Morphological Features of PC12 Cells in Culture—A Light and EM Study," *Brain Res. Bull.*, 18:555–561, 1987.

Hammang et al., "Immortalized Retinal Neurons Derived from SV40 T-Antigen-Induced Tumors in Transgenic Mice," *Neuron*, 4:775–782, 1990.

Hof et al., "Quantitative Analysis of a Vulnerable Subset of Pyramidal Neurons in Alzheimer's Disease: I. Superior Frontal and Inferior Temporal Cortex," *J. Comp. Neuro.*, 301:44–54, 1990.

Hof et al., "Quantitative Analysis of a Vulnerable Subset of Pyramidal Neurons in Alzheimer's Disease: I. Primary and Secondary Visual Cortex," *J. Comp. Neuro.*, 301:55–64, 1990.

Huber et al., "Differences in the Cellular Distributions of Two Microtubule–Associated Proteins, MAP1 and MAP2, in Rat Brain," *J. Neurosci.*, 4:151–160, 1984.

Johnson et al., "Two rat homologues of *Drosophila achaete-scute* specifically expressed in neuronal precursors," *Nature*, 346:858–861, 1990.

Kuwayana et al., "A quantitative correlation of substance P–, calcitonin gene–related peptide–and cholecystokinin–like immunoreactivity with retrogradely labeled trigeminal ganglion cells innervating the eye," *Brain Research*, 405:220–226, 1987.

(List continued on next page.)

Primary Examiner—James Ketter
Attorney, Agent, or Firm—Law Offices of Jane Massey Licata

[57] ABSTRACT

NTera 2/cl.D1 (NT2) cells, a human teratocarcinoma cell line, were manipulated following retinoic acid (RA) treatment to yield >95% pure cultures of neuronal cells (NT2-N cells). This culture method is capable of yielding sufficient highly differentiated post-mitotic NT2-N cells for both biochemical and molecular biological studies. NT2 cells can be transfected efficiently and the transfected gene products can be expressed in both NT2 and NT2-N cells.

8 Claims, 11 Drawing Sheets

OTHER PUBLICATIONS

Lee et al., "Differentiation of NTERA-2 Clonal Human Embryonal Carcinoma Cells into Neurons Involves the Induction of All Three Neurofilament Proteins," *J. Neurosci.*, 6:514–521, 1986.

Lee et al., "Identification of Neural and Adrenal Medullary Surface Membrane Glycoproteins Recognized by Antisera to Cultured Rat Sympathetic Neurons and PC12 Pheochromocyoma Cells," *Neurosci.*, 6:2773–2786, 1981.

Lee et al., "Monoclonal Antibodies Distinguish Several Differentially Phosphorylated States of the Two Largest Rat Neurofilament Subunits (NF–H and NF–M) and Demonstrates Their Existence in the Normal Nervous System of Adult Rats," *J. Neurosci.*, 7:3474–3488, 1987.

Lee et al., "Monoclonal Antibodies to Gel–Excised GlialFilament Protein and Their Reactivities with Other Intermediate Filament Proteins," *J. Neurochem.*, 42:25–32, 1984.

Lendahl et al., "The use of cell lines in neurobiology," *TINS*, 13:132–137, 1990.

Lendahl et al., "CNS Stem Cells Express a New Class of Intermediate Filament Protein," *Cell*, 60:585–595, 1990.

Lindvall, O., "Prospects of transplantation in human neurodegenerative diseases," *TINS* 14:376–384, 1991.

Lo et al., "V–myc Immortalization of Early Rat Neural Crest Cells Yields a Clonal Cell Line Which Generates Both Glial and Adrenergic Progenitor Cells," *Dev. Biol.*, 145:139–153, 1991.

Parysek et al., "Distribution of Novel 57 kDa Intermediate Filament (IF) Protein in the Nervous," *System, J. Neurosci.*, 8:553–563, 1988.

Patel et al., "Expression of the neural cell adhesion molecule in human brain tumors," *Biochem. Soc. Trans.*, 18:264, 1990.

Pleasure et al., "Site–Specific Phosphorylation of the Middle Molecular Weight Human Neurofilament Protein in Transfected Non–neuronal Cells," *J. Neurosci.*, 10:2428–2437, 1990.

Ronnett et al., "Human Cortical Neuronal Cell Line: Establishment from a Patient with Unilateral Megalencephaly," *Science*, 248:603–605, 1990.

Ryder et al., "Establishment and Characterization of Multipotent Neural Cell Lines Using Retrovirus Vector–Mediated Oncogene Transfer," *J. Neurobiol.*, 21:356–375, 1990.

Theodosis et al., "Retention of embryonic features by an adult neuronal system capable of plasticity: Polysialylated neural cell adhesion molecule in the hypothalamo—neurohypophysial system," *Proc. Natl. Acad. Sci. USA*, 88:5494–5498, 1991.

Trojanowski et al., "Distribution of Neurofilament Subunits in Neurons and Neuronal Processes," *J. Histochem. Cytochem.*, 33(6):557–563, 1985.

Trojanowski et al., "Phosphate–Dependent and Independent Neurofilament Protein Epitopes Are Expressed Throughout the Cell Cycle in Human Medulloblastoma (D283 MED) Cells," *Am. J. Pathol.*, 135:747–758, 1989.

Trojanowski et al., "Distribution of Tau Proteins in the Normal Human Central and Peripheral Nervous System," *J. Histochem. Cytochem.*, 37:209–215, 1989.

FIG. 7A
FIG. 7B
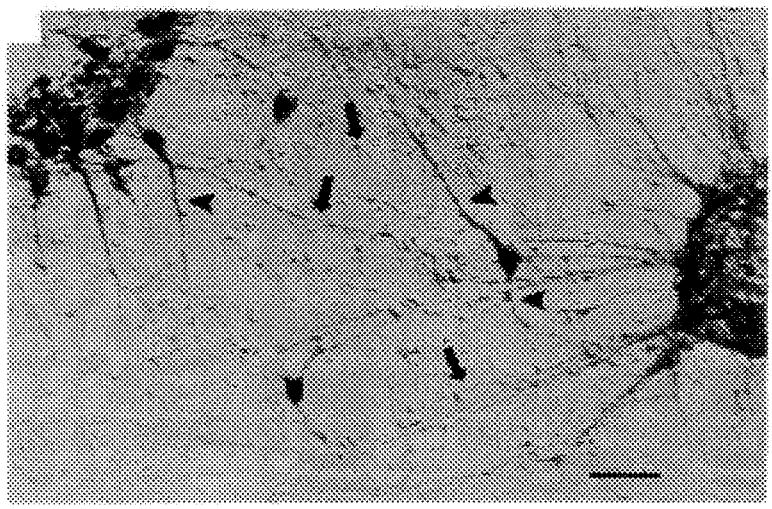
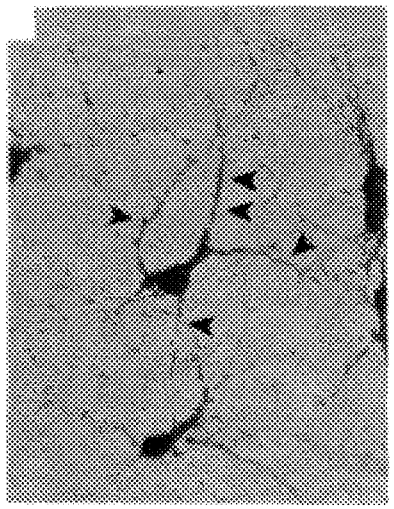

PREPARATION OF PURE CULTURES OF POST-MITOTIC HUMAN NEURONS

CROSS REFERENCE TO RELATED PATENT APPLICATIONS

This is a continuation of application Ser. No. 08/279,268, filed Jul. 22, 1994 abn, which is a Continuation application of U.S. application Ser. No. 08/170,668 filed Dec. 17, 1993, abandoned, which is a Continuation of application of U.S. Ser. No. 07/911,980, filed Jul. 10, 1992, abandoned, which is a Divisional application of U.S. Ser. No. 07/780,715, filed Oct. 21, 1991, issued Dec. 29, 1992 as U.S. Pat. No. 5,175,103.

INTRODUCTION

This invention was made in the course of research sponsored by the NIH grant number NS18616. The Governnent has certain rights in this invention.

BACKGROUND

Mature manmalian neurons are incapable of cell division and cannot, with the exception of olfactory neurons, be generated from stem cells in the adult nervous system. Thus, continuous dividing clonal cell lines with neuronal characteristics have proven to be very useful to neurobiologists studying almost every aspect of the nervous system. Such cell lines allow the generation of large numbers of homogeneous cells and the manipulation of these cells through gene transfer to yield novel derivatives expressing foreign gens products. These advantages have led to the development and characterization of a variety of neuronal cell lines, some of which have been useful for cell biological, biochemical, and molecular biological studies. The utility of these different cell lines and their ability to approximate aspects of the neuronal phenotype vary widely. However, studies conducted over the past decade have shown that the usefulness of a cell line primarily depends on two characteristics: 1) the extent to which a particular cell line resembles post-mitotic neurons; and 2) the doubling time. Frequently, these two key characteristics are inversely related. Many differentiated properties of neurons are not fully articulated in vivo until the stem cell becomes post-mitotic. However, rapidly dividing neuronal cell lines usually do not possess the phenotypic properties of terminally differentiated non-dividing neurons, instead, they often resemble in vivo neuroblasts or embryonic neurons. For example, many of these cell lines elaborate immature neurites with an immature cytoskeleton but lack most of the morphology and neuritic differentiation of post-mitotic neurons. Nevertheless, since they divide rapidly, these cell lines are useful for biochemical and transfection experiments. Naturally occurring neoplastic derivatives of many neuronal cell types of the central (CNS) and peripheral (PNS) nervous systems usually fall in this category (e.g., neuroblastomas, pheochromocytomas and medulloblastomas). At the other end of the spectrum are cell lines exemplified by HCN 1 (Ronnett et al., 1990, Science, 248:603–605). These cells have many characteristics of differentiated neurons, but they divide so slowly (i.e., doubling time of 72 hours when undifferentiated) that they are not amenable to many experimental manipulations. Even PC 12 cells, the classic example of a neuronal cell line, revert to their less neuronal, rapidly dividing phenotype upon removal of NGF (Greene and Tischler, 1982, *Advances in Cellular Neurobiology*, S. Federoff and L. Hertz, eds., Academic Press, New York).

Recently, considerable effort has been expended to immortalize specific neuronal precursors that are found transiently during development (for recent reviews, see Cepko, Ann. Rev. Neuro., 12:47–65, 1989; or Lendahl and McKay, TINS, 13:132–137,1990; and, for specific examples see, Bartlett et al., Proc. Natl. Acad. Sci. USA, 85:3255-3259, 1988; Fredericksen et al., Neuron, 1:439–448, 1988; Bitten et al., Neuron, 4:189–201 (1990); Hammang, et al, Neuron, 4:775–782, 1990; Ryder et al., J. Neurobiol., 21:356–375, 1990; Lo et al., Dev. Biol., 145:139–153, 1991). This approach is particularly valuable because these cell lines seem to approximate characteristics of specific cell types at particular stages of development. Already, new molecules which may serve important developmental functions have been isolated using these novel cell lines (Johnson et al., Nature, 346:858–861, 1990; Lendahl et al., Cell, 60:585–595, 1990). However, with the exception of MAH cells (Birren et al., Neuron 4: 189–201, 1990), cell lines generated using this strategy have a limited ability to undergo further neuronal differentiation. Rather, they seem to be more useful for examining specific branch points in the emergence of neuronal lineages.

The ideal cell line for analysis of the processes of neuronal maturation and the intrinsic factors which affect the establishment of the neuronal phenotype would be one that divides rapidly so that it could be grown in large quantities and transfected to produce a stable population of cells expressing exogenous gene products. Upon induction with an agent promoting differentiation, this ideal cell line would leave the cell cycle, undergo an irreversible commitment to a neuronal phenotype, and exist in a stable post-mitotic state. These cells would subsequently elaborate extensive neuritic processes and would mature to a state similar to that of primary neurons in culture.

Embryonal carcinoma cell lines satisfy some of the above criteria. These cells, which have been derived from both murine and human embryonal tumors, consist of undifferentiated multipotential cells which will differentiate into one or several cell types when placed under certain conditions (usually including treatment with retinoic acid [RA]). This process resembles the actual commitment to different phenotypes which are found in vivo. These cell types frequently include neurons, glial, muscle, and/or endothelial cells at various stages of differentiation. Thus, their usefulness to neurobiologists is limited by their heterogeneity. NTera 2/D1 (NT2), a human teratocarcinoma cell line, has characteristics in common with its murine counterparts in that they are capable of undergoing phenotypic changes in response to RA. However, unlike most of the murine embryonal carcinoma cell lines, the only identifiable phenotype found following RA treatment of NT2 cells are neurons (Andrews, Dev. Biol., 103:285–293 (1984); Andrews et al., Lab. Invest., 50:147–162 (1984); Lee and Andrews, J. Neurosci., 6:514–521 (1986). Unfortunately, in all previous studies, these neurons represented only a small percentage of the cells, and they coexisted with a large unidentified population of dividing large flat cells and a residual number of undifferentiated stem cells (Andrews, 1984).

SUMMARY OF THE INVENTION

Treatment with retinoic acid and primary culture techniques (including differential attachment to tissue culture plastic and treatment with mitotic inhibitors) are used to obtain highly purified populations of neurons from a human teratocarcinoma cell line. This culture method is capable of yielding highly differentiated post-mitotic cells. When undifferentiated cells were transfected with a β-galactosidase (β-gal) expression plasmid, β-gal expression was shown to be present in both undifferentiated and post-mitotic cells. Thus, transfection of expression plasmids into undifferentiated cells allows the introduction of exogenous gene products into cells which can then be induced to become stable, post-mitotic human neurons.

DESCRIPTION OF DRAWINGS

FIG. 7: $^3$H-uridine labeling of NT2-N cell cultures five weeks after Replate #2. A (low power) and B (high power) are photomicrographs of NT2-N cells produced using Hoffman Modulation Contrast optics. The labeled cells and processes appear dark grey or black because of the silver grains from the NTB-2 emulsion autoradiography. A shows a field of cells containing labeled cell bodies and dendritic processes (arrowheads) with many unlabeled axonal processes (some examples are shown with arrows) arising from the clumps of cells in the field and elsewhere on the culture dish. B shows a higher power micrograph of several cells. The dendritic processes of one of these cells have been indicated using arrowheads. The bar in A is 50 µm when applied to A, and 100 µm when applied to B.

DESCRIPTION OF THE INVENTION

A human teratocarcinoma cell line (NTera 2/Cl. D1 or NT2 cells) was manipulated following treatment with retinoic acid (RA) to yield greater than 95% pure cultures of neuronal cells (NT2-N cells).

Figure 1:
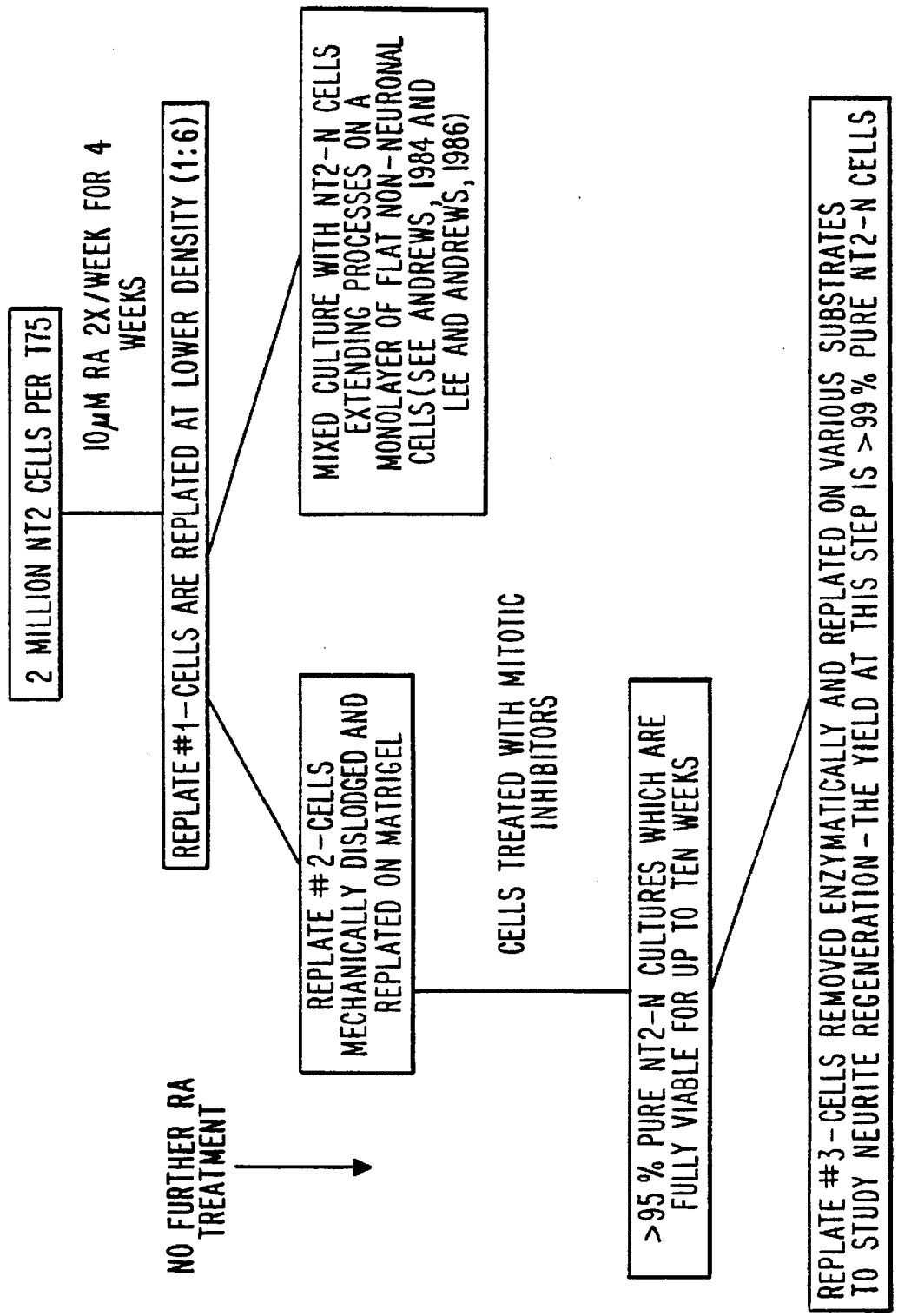
FIG. 1 is a schematic showing the method for generation of pure cultures of NT2-N cells from RA treated NT2 cells.
Figure 2A:
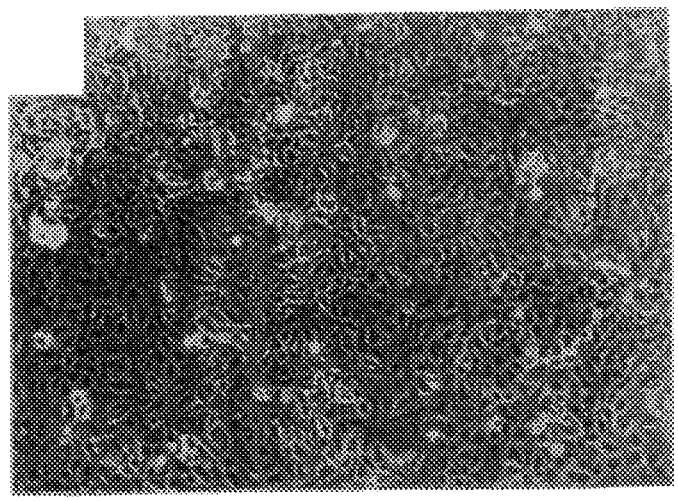
FIGS. 2A–F are phase contrast photomicrographs showing the morphologic changes which occur during the course of the method shown in FIG. 1: A, untreated NT2 cells; B, NT2 cells following Replate #1 (note the round, phase bright cells in clumps sitting above the adherent cells below); C, 1 day following Replate #2 (note that many cells have begun to elaborate rudimentary processes similar to a number of human neuroblastoma cell lines); D, 7 days following Replate #2 (the non-neuronal cells have begun to die off and the cultures are now dominated by neuron-like NT2-N cells); E, 30 days following Replating #2 (note that most cells exhibit the morphology of neurons and have migrated into large aggregates and that extensive process outgrowth has occurred; F, high power photomicrograph of NT2-N cells showing the typical neuronal morphology of these cells. The arrows point to the long thin untapering process resembling an axon emanating from a cell in FIG. 2F. The arrowheads point to the two major processes which resemble dendrites. The bar in E applies to A–E and equals 200 µm and the bar in F equals 30 µm.
Figure 2B:
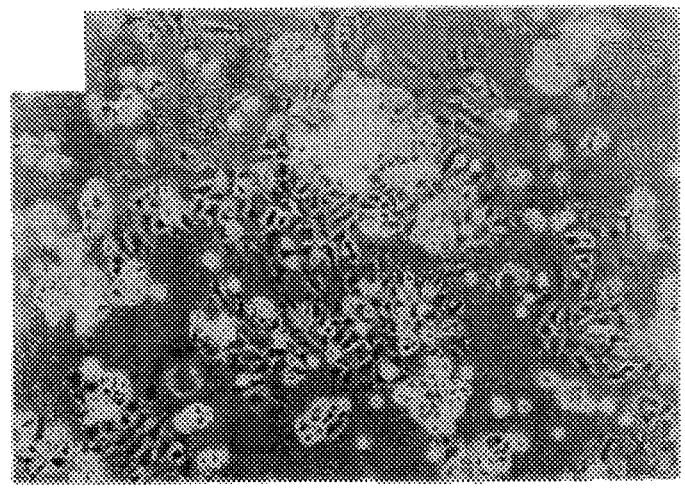
Figure 2C:
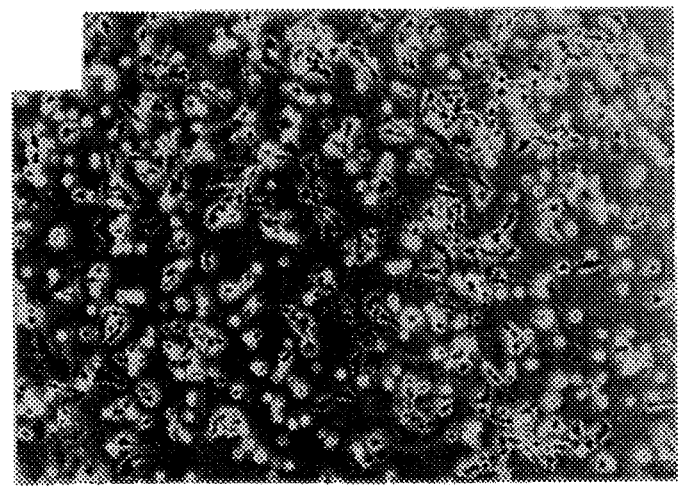

The generation of these highly purified cultures of stable post-mitotic cells is schematically outlined in FIG. 1. When undifferentiated NT2 cells were initially plated, they appeared as phase dark cells with a granular appearance (FIG. 2A). Following four weeks of RA treatment, the cells formed an extremely dense multi-layered culture. These cultures were then dispersed and replated at a lower density to release the NT2-N cells buried in the midst of the many layers of cells. Following this treatment, the NT2-N cells were seen as small phase bright cells above a layer of flat cells (Replate #1; FIG. 2B). The derivation, differentiation paradigm, and early morphological appearance of NT2 cells following treatment with RA to this point (i.e., Replate #1) were examined in detail previously (Andrews et al., 1984; Andrews, 1984). Approximately 5% of the cells after Replate #1 are neurons as judged by the presence of neuron specific markers. To further enrich for these neurons, we took advantage of the fact that the small phase bright NT2-N cells were loosely attached to the layer of flat cells after Replate #1 cultures and could be mechanically dislodged and enriched. This treatment (Replate #2), yielded a culture consisting primarily of small rounded phase bright cells, some of which had short processes reminiscent of human neuroblastoma cell lines (FIG. 2C). This step led to an approximately fourfold enrichment of the neuronal cells as assayed by the measurement of neuronal specific enzymes. These cultures also contained some flat cells, which resembled undifferentiated NT2 cells, which, when allowed to grow unchecked, gradually formed a monolayer with the small, phase bright cells sitting on top. After Replate #2, the phase bright NT2-N cells grew numerous processes and formed large cellular aggregates within two weeks and were viable for up to five months without ever showing any phenotypic reversion as determined by the continuous presence of neuron specific markers. However, these cultures were not a significant improvement over the mixed cultures derived from Replate #1 because of the presence of the contaminating monolayer of flat cells. To eliminate these dividing flat cells, the cultures were treated with a combination of mitotic inhibitors following Replate #2. This treatment had no effect on the NT2-N cells, but it completely suppressed the growth of the flat cells. Hence, nearly all of the flat cells were eliminated, leaving behind a very small number of mitotically poisoned cells with extensive cytoplasm. By two weeks of treatment, about 95% of the cells were differentiated neurons, i.e., NT2-N cells. We confirmed this observation, obtained roughly from phase contrast microscopy, by double-staining cultures of cells using monoclonal antibodies (mAb) specific for either the undifferentiated NT2 cells (Cam5.2 which reacts with keratins 8 and 18) or the NT2-N cells (rabbit anti-NF-L which reacts exclusively with the low molecular weight neurofilament protein). These experiments showed large numbers of NT2-N cells stained with the NF-L antiserum and only very occasional flat cells with extensive cytoplasm stained with Cam5.2. When cultured on Matrigel, which served as a better substrate for these cells than poly-D-lysine or poly-D-lysine and laminin, these nearly pure cultures of NT2-N cells were viable for about 10 weeks.

Figure 2D:
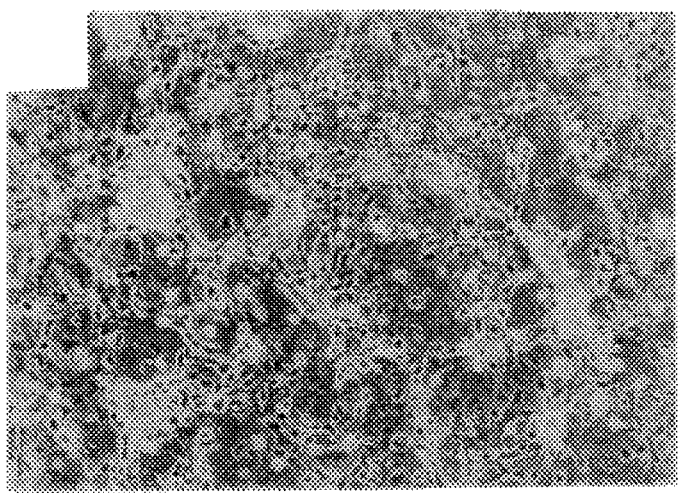
Figure 2E:
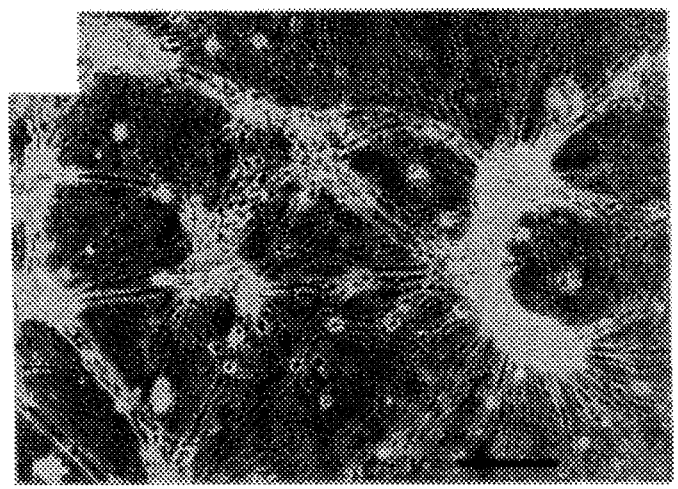
Figure 2F:
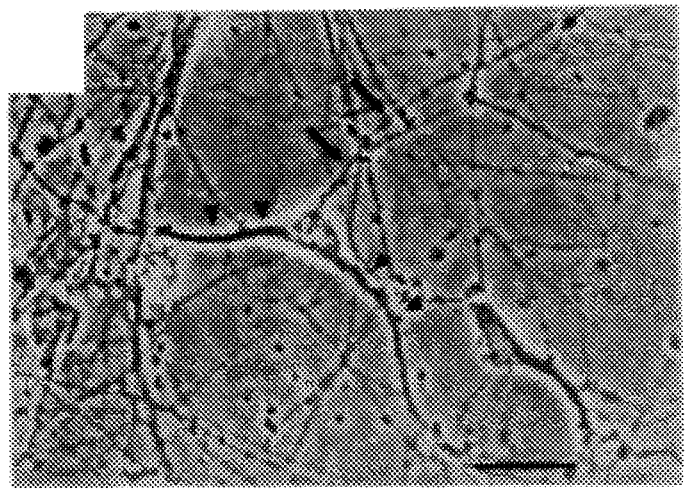

When these cultures were examined using phase contrast microscopy at various times (FIGS. 2D & E), progressive development of extensive neuritic networks covering the entire culture dish was observed. Fine untapering long processes, similar to the axonal processes described in primary neuronal cultures, were also evident. As shown in FIG. 2F, single cells in these cultures elaborated processes that were thick at the base and tapered progressively from the cell body (arrowheads in FIG. 2F). Additionally, thin untapering processes arose from these cells (arrows in FIG. 2F). These two morphologically distinct types of processes resembled the dendrites and axons, respectively, of primary cultures of CNS and PNS neurons. The identity of these two classes of processes as axons and dendrites was borne out by molecular markers of axons and dendrites they expressed (See FIGS. 6 and 7). During this period of extensive process outgrowth, the NT2-N cells displayed growth cones typical of primary cultures of neurons from various regions of the nervous system. Another consistent feature of pure NT2-N cells was their motility. Initially, NT2-N cells were evenly dispersed over the entire surface of the culture dish (FIG. 2C), but over time they migrated together to form cellular aggregates with large interconnecting fascicles of axons (FIG. 2D). If the cells were plated on poly-D-lysine either alone or with laminin, they formed even larger aggregates that resembled explanted ganglia.

We examined the reproducibility of this new method to generate large numbers of NT2-N cells by recording the number of cells harvested from Replate #2 in a series of experiments. Over a number of trials (n=9), beginning with a T75 culture flask seeded with $2 \times 10^6$ NT2 cells, treated with $1 \times 10^{-5}$ M RA for four weeks and then taken through Replates #1 and #2, we recovered an average of $48.9 \times 10^6$ cells (s.e.m. $3.3 \times 10^6$, n=9). Despite limitations in available techniques to estimate the number of NT2-N cells, our quantitative data indicate that approximately 20% of the cells recovered after Replate #2 were NT2-N cells. Thus, the average yield per T75 is about $10 \times 10^6$ cells. To date, this culture method has been reproduced at a weekly interval for almost 2 years.

Figure 3A:
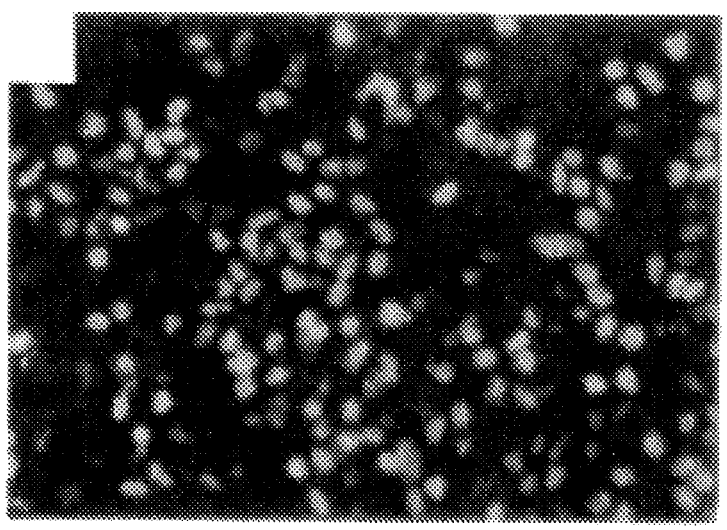
FIGS. 3A–C show the results of BrDU labeling of NT2 and NT2-N cells. A, Undifferentiated NT2 cells labeled with BrDU and stained with BU-1. B, NT2-N cells labeled with BrDU and stained with BU-1. C, the same field as B labeled with an anti-NF-L antiserum. The bar in C is 200 µm.
Figure 3B:
Figure 3C:
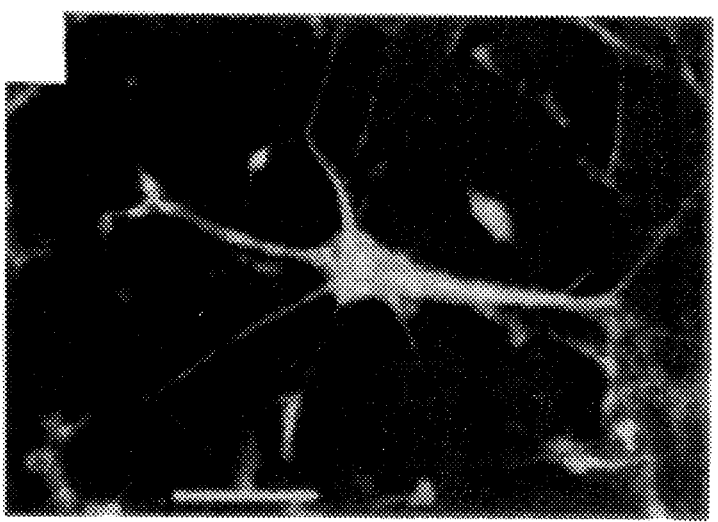

In order to demonstrate that NT2-N cells were incapable of cell division, cultures of both NT2-N cells and undifferentiated NT2 cells were incubated with bromodeoxyuridine (BrDU), and labeled nuclei were visualized by indirect immunofluorescence using a mAb to BrDU incorporated into DNA. More than 50% of the nuclei from undifferentiated cells were immunostained by the mAb after three hours of BrDU labeling (FIG. 3A). In contrast, there were no labeled NT2-N nuclei in pure Replate #2 cultures (FIG. 3B), nor was there labeling after 20 hours exposure. The same cells were also stained with an antiserum against NF-L to show that NT2-N cells are present in the field (FIG. 3C). Furthermore, visual inspection of NT2-N cells, either in pure cultures after withdrawal from mitotic inhibitors, or in mixed cultures, never detected an increase in the number of neuronal cells. In fact, we have followed single clumps of NT2-N cells over three months and we have not detected an increase in cell number despite the absence of mitotic inhibitors and the presence of 10% fetal bovine serum in the medium for the entire culture period. Taken together, these data suggest strongly that NT2-N cells are post-mitotic.

Figure 4A:
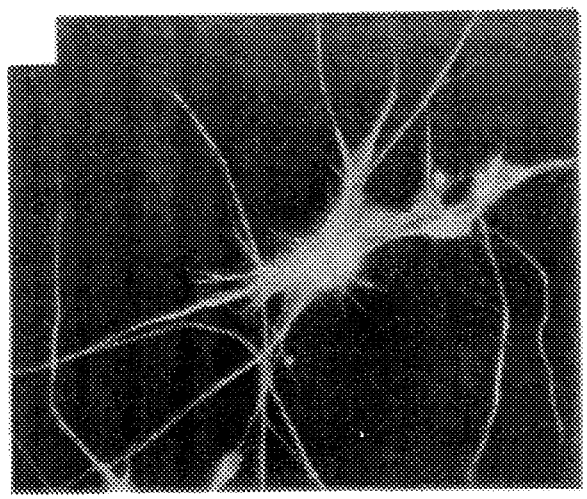
FIGS. 4A–F show immunocytochemistry results demonstrating the expression of neuronal markers in NT2-N cells: A and B, double labeling with RM0254, a mouse anti-NF-M mAb, and anti-NF-66, a rabbit antiserum raised against NF-66; C, 1WM 3G5, a mouse anti-MAP1b mAb; D, AP14, a mouse anti-MAP2 mAb; E, $A_2B_5$, a mouse mAb specific for a ganglioside found on many neurons; F, T14, a mouse anti-tau mAb. The bar in F is 30 µm.
Figure 4B:
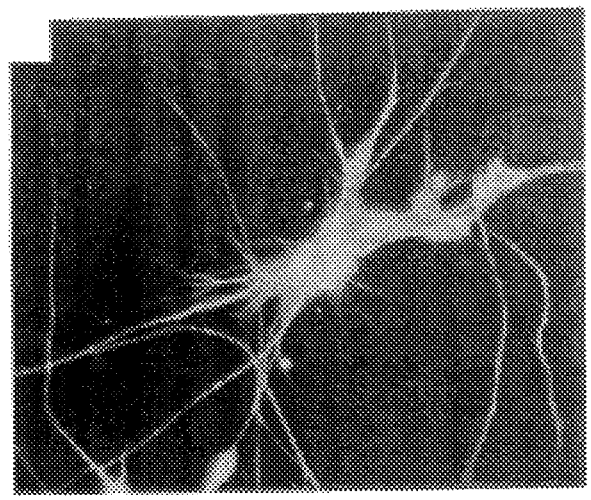
Figure 4C:
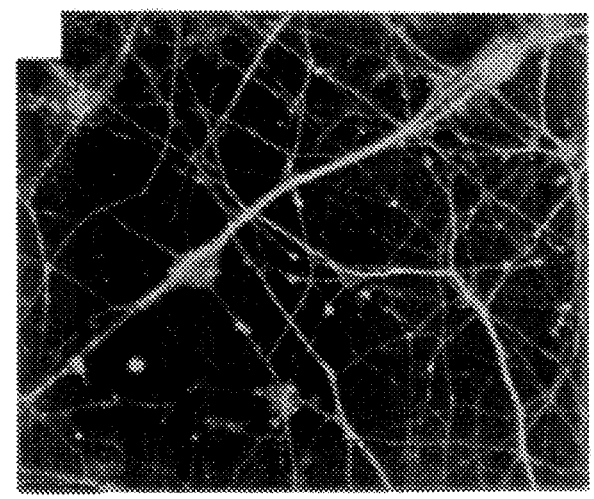
Figure 4D:
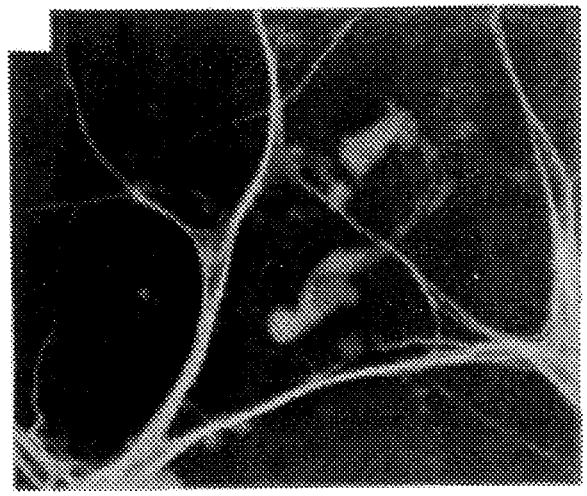
Figure 4E:
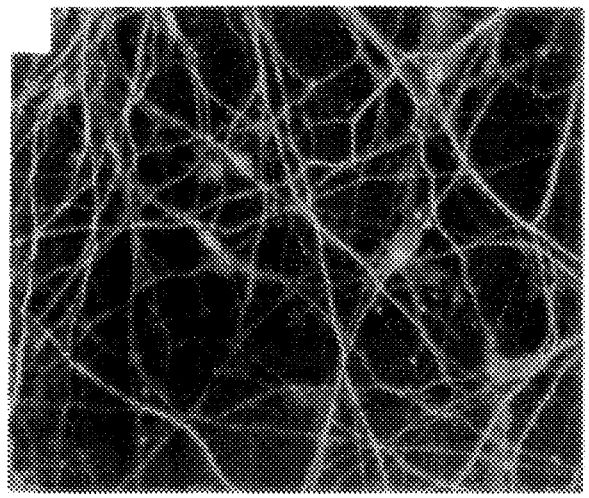
Figure 5:
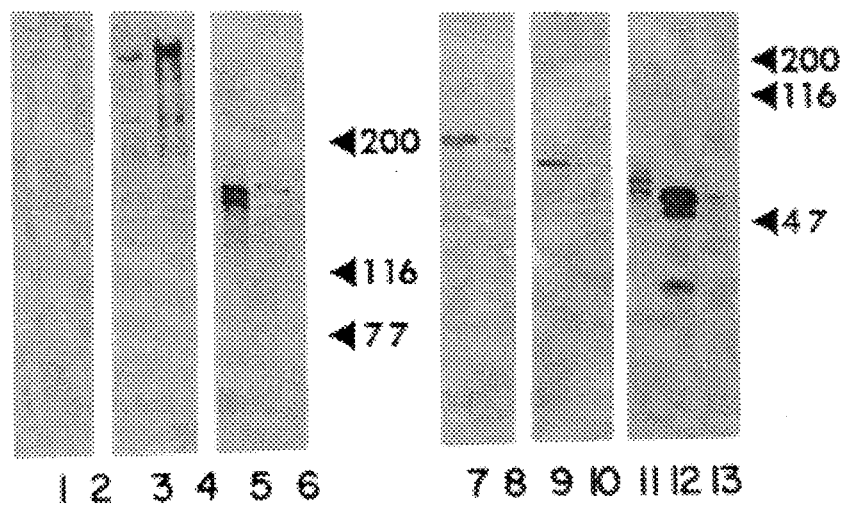
FIG. 5 shows the results of immunoblot analysis of the expression of cytoskeletal markers in NT2-N cells. Lanes 1–6 are from 6% SDS-PAGE gels and lanes 7–13 are from 10% SDS-PAGE gels. 1, 20 µg of cytoskeletal extract from NT2-N cells and 2, bovine MAPs blotted with 1WM 3G5, an anti-MAP1b mAb. 3, 20 µg of cytoskeletal extract and 4, bovine MAP2 blotted with AP14, an anti-MAP2 mAb. 5, 10 µm of cytoskeletal extract and 6, human nerve root IF preparation blotted with RM0254, an anti-NF-M mAb. 7, 20 µg of cytoskeletal extract and 8, human nerve root intermediate filament preparation blotted with anti-NF-L, an antiserum raised to a human NF-L. 9, 20 µg of cytoskeletal extract and 10, bovine NF-66 blotted with anti-NF-66 an antiserum raised to rat NF-66. 11, purified adult human tau; 12, purified human fetal tau and 13, 60 µg of cytoskeletal extract blotted with T14, an anti-tau mAb. MW markers are kD as indicated.

Previous studies estimated that routine cultures of NT2-N cells (i.e., cultures derived from Replate #1—see FIG. 1) make up a minor component of the total cell population (Andrews, 1984; Lee and Andrews, 1986). These cells were shown previously to express neurofilament proteins (Andrews, 1984; Lee and Andrews, 1986), the antigen recognized by $A_2B_5$ (a mAb recognizing a cell surface glycolipid characteristic of neurons and some glial cells), and to possess tetrodotoxin sensitive Na+ channels (Rendt et al., 1989). We have confirmed and extended many of these findings using pure cultures of NT2-N cells in studies designed to examine the expression of several markers typical of neurons in vivo and in vitro (Table I). In addition to the well known neurofilament triplet proteins (Table I; FIGS. 3C, 4A, and FIG. 5), NT2-N cells expressed NF-66 (also known as alpha-internexin; FIG. 4B) but not peripherin (Table I), the two more recently described members of the neuronal intermediate filament family. NT2-N cells, therefore, may resemble CNS neurons because NF-66 is abundant only in the CNS, and peripherin is found in virtually all PNS neurons. NT2-N cells also expressed several neuronal microtubule associated proteins (MAPs) i.e., MAP1A, MAP1B, MAP2, and tau (Table I; FIGS. 4C, D & F). Neuronal membrane or membrane associated antigens were also expressed by NT2-N cells. These included the antigen recognized by $A_2B_5$ (FIG. 4E), NCAM (another cell surface molecule frequently expressed by neurons and neuronal neoplasms) and GAP43 (a growth associated protein concentrated in growth cones). We also found that NT2-N cells expressed markers of secretory activity typical of neurons and neuroendocrine cells (e.g., synaptophysin and chromogranin; Table I). Synaptophysin is a marker for small transparent synaptic vesicles which store and release classical neurotransmitters, and chromogranin is a marker for larger dense-cored vesicles which are involved in neuropeptide and catecholamine biosynthesis.

Table I represents the results obtained when NT2-N cells were examined with a number of antibodies specific for the proteins shown in the first column. The (+) symbol indicates that the antibody stained and/or blotted the released protein in NT-2N cells. The (−) symbol indicates that the relevant antibody does not stain NT2-N cells.

TABLE I

Markers of the neuronal phenotype of NT2-N cells

| Protein | Antibody | Result | Reference or Source of Antibody |
|---|---|---|---|
| NF-L | rabbit anti-NF-L | + | Trojanowski et al., Am. T. Pathol. 135:747–758 (1989) |
| NF-M | RMO254 | + | Lee et al., T. Neurosci., 7:3474–3488 (1987) |
| NF-H | RMO24 | + | Lee et al., J. Neurosci., 7:3474–3488 (1987) |
| NF-66 | rabbit anti-NF-66 | + | Chui et al., Neuron, 2:1435–1445 (1989) |
| vimentin | rabbit anti-vimentin | +* | Pleasure et al., J. Neurosci., 10:2428–2437 (1990) |
| peripherin | rabbit anti-peripherin | − | Parysek et al., J. Neurosci., 8:55–63 (1988) |
| GFAP | 2.2B10 | − | Lee et al., J. Neurochem., 42:25–32 (1984) |
| Keratins 8 and 18 | Cam5.2 | − | Becton Dickinson |
| MAP1A | HM1 | + | Huber and Matus, J. Neurosci., 4:151–160 (1984) |
| MAP1B | 1WM3G5 | + | L. Binder, unpublished |
| MAP2 | AP14 | + | Geisert et al., Proc. Natl. Acad. Sci. USA, 87:3967–3971 (1990) |
| tau | T14 | + | Trojanowski et al., J. Histochem. Cytochem., 37:209–215 (1989) |
| synaptophysin | SY-38 | + | Boehringer Mannheim |
| chromogranin | LKH110 | + | Boehringer Mannheim |
| GAP-43 | 9-1E10 | + | Goslin et al., J. Neurosci., 10:588–602 (1990) |
| $GT_3$ | $A_2B_5$ | + | Dubois et al., J. Biol. Chem., 265:2797–2803 (1990) |
| N-CAM | ERIC-1 | + | Patel et al., Biochem. Soc. Trans., 18:264 (1990) |
| PSA-NCAM | MenB | + | Theodosis et al., Proc. Natl. Acad. Sci U.S.A. (1991) |
| L1 (NILE) | Guinea pig anti-NILE | + | Lee et al., Neurosci., 6:2773–2786 (1981) |

*Rabbit anti-vimentin is positive on Western blots of NT2-N cell extracts but does not stain these cells by indirect immunofluorescence. This antiserum is capable of staining vimentin in other cells (including the undifferentiated NT2 cells) therefore, it seems likely that the large amount of NF proteins assembled in the same filaments with vimentin masks the reactivity of vimentin in NT2-N cells.

Immunochemical studies were conducted to confirm the expression of several of the markers mentioned above (FIG. 5) as well as to demonstrate the feasibility of using NT2-N cells for biochemical studies. Using gel replicas of NT2-N cytoskeletal extracts, we confirmed that MAP1B, MAP2, tau, NF-L, NF-M and NF-66 were indeed present in these cells. Coomassie blue stained gels, together with the immunoblot in FIG. 5, shows that MAP2 in NT2-N cells comigrates with the lower of the two isoforms of bovine MAP2. Because of its sensitivity to proteolysis, MAP2 has never been identified biochemically from human tissue. Nevertheless, we believe that the MAP2 from NT2-N cells is likely to be MAP2b, a less phosphorylated form of MAP2, which predominates during development and corresponds to the more rapidly migrating of the two MAP2 polypeptides in the bovine MAP2 preparations. FIG. 5 also shows that the tau found in NT2-N cells corresponds to the fetal forms rather than the adult forms of tau. Fetal tau is translated from differentially spliced forms of tau mRNA which are predominant during embryonic life. MAP1B (also known as MAP5) is also an embryonic MAP which persists into adulthood but at greatly reduced levels. NT2-N cells express low levels of MAP1A and NF-H (Table I), two proteins which are up regulated in their expression during development, but which only achieve their highest levels in adult nervous systems, including that of humans. This finding, together with the expression of three embryonic MAPs and NF-66, implies that the cytoskeleton of NT2-N cells resembles that of embryonic CNS neurons.

Among the most identifiable and highly differentiated features of neurons is their highly polarized phenotype. Neurons typically have a single axon and multiple dendrites which can be distinguished by their morphology, by the organelles they contain and by several differentially distributed molecular markers. For example, the cell body and dendrites (somato-dendritic domain) have ribosomes (and thus contain RNA) while axons (axonal domain) lack ribosomes. Further, the microtubules in dendrites are oriented in both directions while those in axons have their (+) end oriented distally. Finally, axons are rich in highly phosphorylated NF proteins and tau, while cell bodies and dendrites have primarily hypophosphorylated variants of NF proteins. These differences are all likely to contribute to the distinct functions of dendrites as primarily post-synaptic processes and of axons as projecting pre-synaptic processes.

Figure 6A:
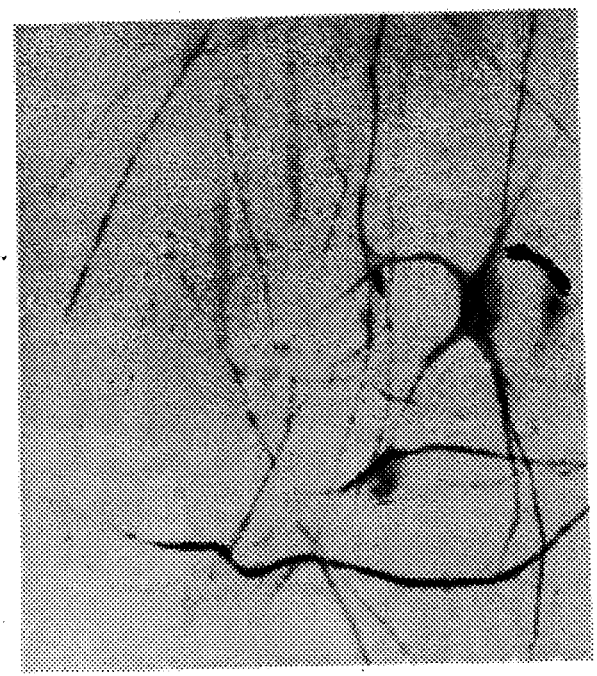
FIG. 6: Confocal microscopy of NT2-N cells stained with markers for axons and dendrites. A and B show microscopic fields stained with HO14 (green) and RMdO 20 (red). HO14 is a rat mAb specific for the highly phosphorylated forms of NF-M while RMdO20 is a mouse mAb specific for the poorly phosphorylated forms of NF-M. C. shows a high power field of cells stained with HO14 and AP14, a mouse mAb specific for MAP2. These images were generated by collecting separate data for each channel and then merging them and imparting them with computer generated pseudo-color. The bar in C is 25 µm when applied to C, and is 50 µm when applied to A and B.
Figure 6B:
Figure 6C:
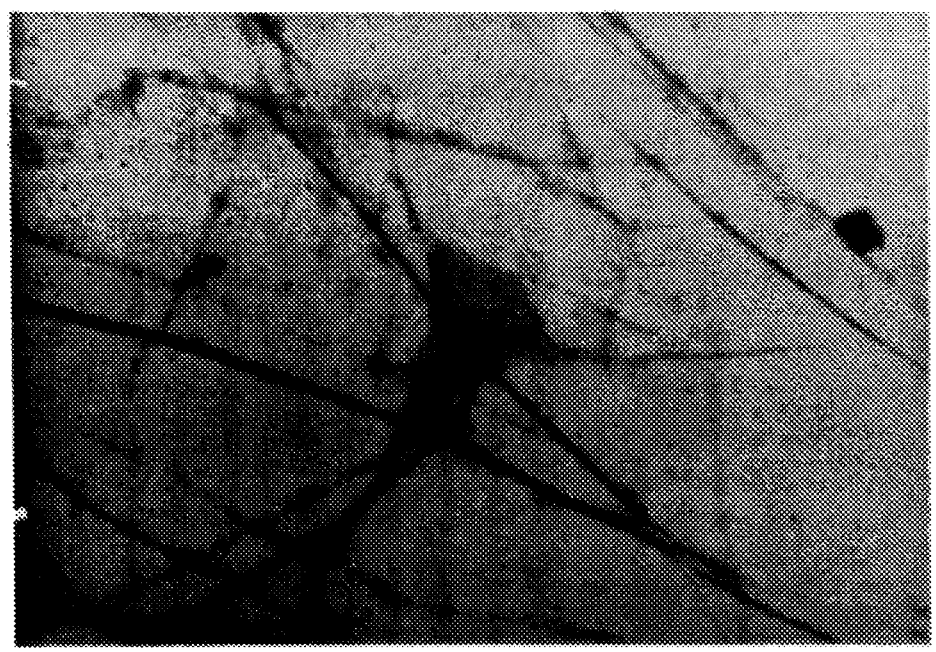

Because of the highly polarized morphology of NT2-N cells after 3–4 weeks in culture, we decided to examine whether the processes of NT2-N cells can be differentiated into axons and dendrites. Indeed, when we examined the distribution of phospho-isoforms of NF-M in NT2-N cells, using confocal microscopy, we found that highly phosphorylated NF-M is found preferentially in the long thin processes emanating from NT2-N cells while hypophosphorylated NF-M is found in the cell body and short tapering processes (FIGS. 6A and 6B). MAP2 is also localized exclusively in the cell soma and the short processes of NT2-N cells (FIG. 6C). The non-overlapping distribution of these proteins is very clearly seen using the computer generated superimposed pseudocolor images in FIG. 6. The somato-dendritic domains of the cells were stained (in red) by the mAbs against hypophosphorylated NF-M (RMdO20—FIGS. 6A and 6B) and MAP2 (AP14—FIG. 6C) but were unstained by HO14 (in green), a mAb specific for highly phosphorylated NF-M. Conversely, the axons passing through the fields shown in FIG. 6 were only stained with HO14.

Figure 4F:
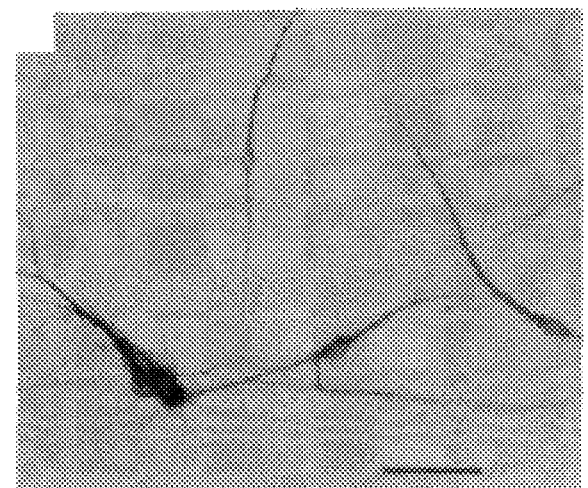

A more directly functional feature of the dendrites was examined to determine if NT2-N cells possessed functioning dendrites. As mentioned above, dendrites accumulate ribosomes so that they can respond rapidly to synaptic signals with changes in protein synthesis. This makes it possible to use 3H-uridine to label dendritic processes in neurons in culture. This technique was used to label NT2-N cells and found that, following emulsion autoradiography, processes resembling dendrites are indeed darkly labeled with silver grains while long projecting untapered processes remain unlabeled (FIG. 7). This demonstrates that NT2-N cells do indeed possess identifiable dendrites and axons as determined by several criteria. One interesting point is the localization of tau throughout the cell body, dendrites and axons in NT2-N cell (FIG. 4F). This is distinct from the finding in sympathetic and cerebral neurons in culture but is quite similar to what has been observed in hippocampal neurons. Thus, while it is clear that tau is necessary for axonal elongation in some neurons in culture (perhaps only in those where tau is restricted to axons) additional studies will be necessary to determine the functional role of tau in axons. This peculiarity of NT2-N cells and hippocampal neurons may be related to their expression of fetal tau rather than adult tau.

Figure 8A:
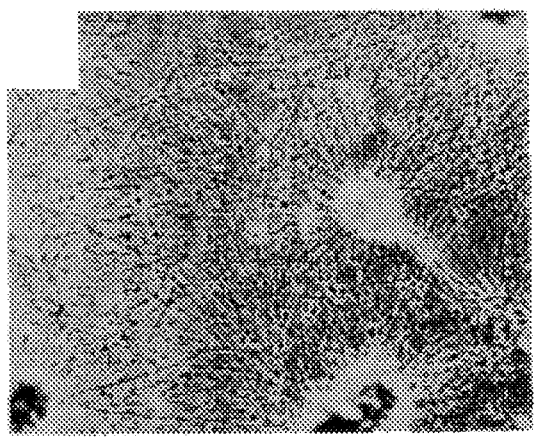
FIGS. 8A–D are photographs showing neurite regeneration following Replate #3. A, NT2-N cells grown on Matrigel for one week following Replate #3. B, NT2-N cells grown on poly-D-lysine for one week following Replate #3. The arrow in FIG. 6D points to a flat non-neuronal cell. The bar in D refers to A, B, and D and is 200 µm. The bar in C is 30 µm.
Figure 8B:
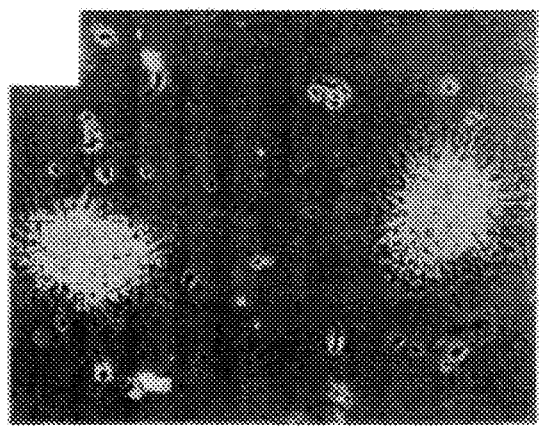
Figure 8C:
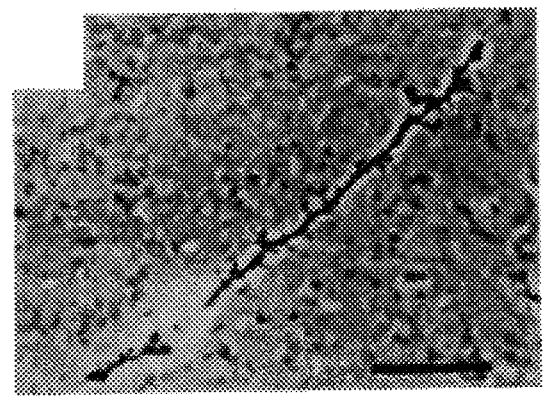

Since NT2-N cells may be a model for immature CNS neurons, studies were conducted to assess their plasticity. When pure cultures of NT2-N cells (cells grown for 1–3 weeks following Replate #2) were enzymatically detached and replated again (Replate #3) they rapidly re-extended neurites. These processes continued to elongate until a dense network of neurites was formed by one week following replating (FIG. 8A). The rapid elaboration of neurites and the eventual formation of the network of processes was found to be highly dependent on the substratum used. For example, rapid outgrowth occurred on cells grown on poly-D-lysine plus laminin or Matrigel substrates but not on poly-D-lysine alone. FIG. 8B illustrates cell clumps grown on poly-D-lysine alone. Even after seven days, these cells had very short processes which ended in flat broad growth cones. By twenty hours, the NT2-N cells on Matrigel began to elaborate their processes (FIG. 8C). These differential effects of Matrigel (or laminin) and poly-D-lysine on neurite regrowth in NT2-N cells are consistent with the well known neurite-outgrowth promoting effects of laminin on a variety of PNS and CNS neuronal cells in culture. The ability of NT2-N cells to regenerate neurites after multiple replating shows that they retain the plasticity of immature neurons. Furthermore, Replate #3 affords us a means to obtain more pure cultures of NT2-N cells (at least 99%) which will allow us to pursue experiments in the future which depend on the availability of purer cultures.

Figure 8D:
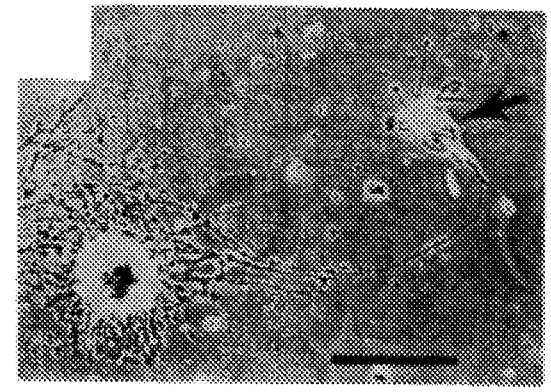

In addition to the substratum, non-neuronal cells played a role in promoting neurite outgrowth; this is most evident in Replate #3 cultures. We observed that NT2-N cells replated on poly-D-lysine alone were clustered around the extremely rare non-neuronal cells found in these cultures, and that many neurites from the clump of NT2-N cells extended directly toward the non-neuronal cells. A dramatic example of this phenomena is shown in FIG. 8D in which several processes appear to have changed direction dramatically in order to grow toward the non-neuronal cell. Repeated observation of the cells in FIG. 8D revealed that the neurites retracted completely following the death of the non-neuronal cell. This result implies that residual non-neuronal cells may release a diffusible substance which is chemotropic for NT2-N cells. Similarly, the presence of non-neuronal cells may explain the extended viability of NT2-N on a non-neuronal cell monolayer (up to five months) compared to the pure NT2-N cell cultures (eight to ten weeks). Taken together, these studies suggest a role for non-neuronal cells in promoting both the survival of NT2-N cells and neurite extension.

Figure 9A:
FIGS. 9A–C are photographs showing β-gal expression of NT2-SPUD cells visualized by X-gal histochemistry using Hoffman modulation contrast microscopy. A, NT2-SPUD cells before RAtreatment. B and C, NT2-SPUD cells after Replate #2. The bar in C is 100 µm when applied to A and C and is 50 µM when applied to B.
Figure 9B:
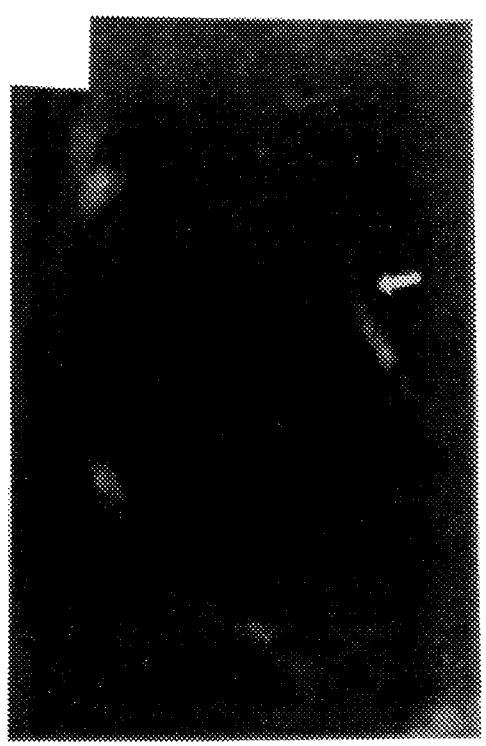
Figure 9C:
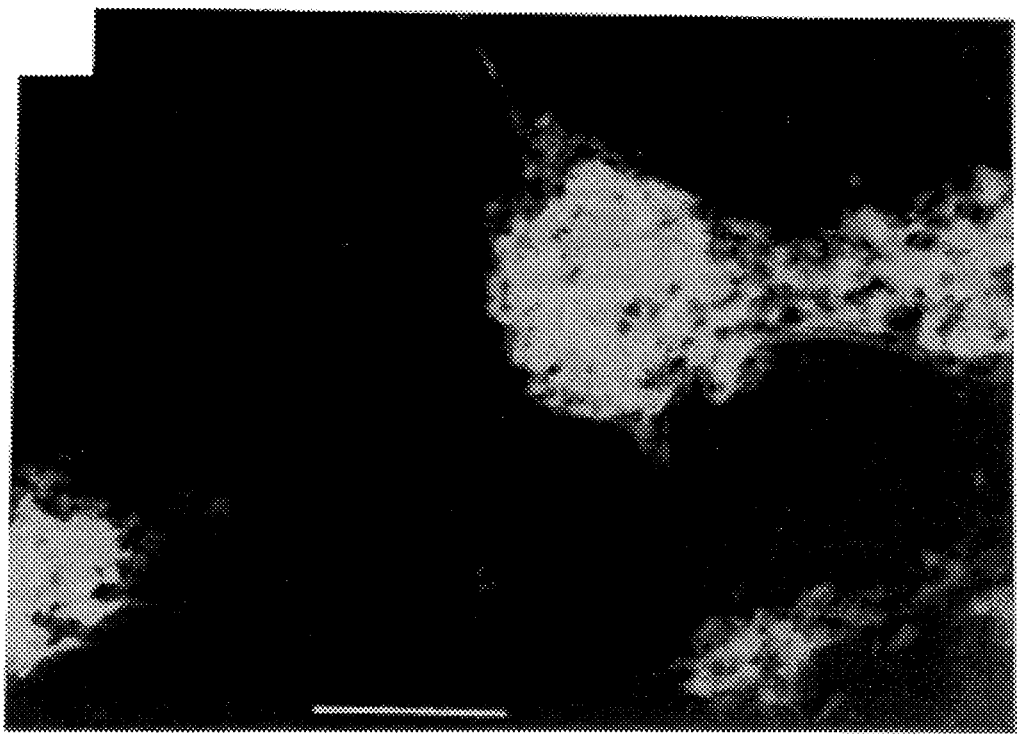

To assess the utility of NT2-N cells for gene transfer experiments, we stably transfected undifferentiated NT2 cells with SPUD1, a β-galactosidase (β-gal) expression plasmid. These studies were designed to determine whether NT2-N cells would continue to express the exogenous protein product following differentiation with RA. When SPUD1 was cotransfected with pSV2neo (used as a selectable marker) into undifferentiated NT2 cells, we derived a G418 resistant population of cells which expressed β-gal as assayed by histochemical staining (FIG. 9A). Upon stimulation of these NT2-SPUD cells with RA, following the same protocol as described in FIG. 1, we were able to derive pure cultures of β-gal positive NT2-N cells (FIGS. 9B & C). The blue reaction product indicating the presence of β-gal protein was concentrated in the cell soma and only extended into the processes of some of the NT2-N cells (see arrows in FIG. 9B). The β-gal reaction product appeared to be concentrated in granular aggregates throughout the cell body (FIG. 9B). This finding suggests that NT2-N cells will continue to express exogenous gens products introduced into NT2 cells.

We have shown that NT2 cells closely approximate the research criteria of an ideal neuronal cell line. Our observations on the NT2-N cells and the novel methods developed for their culture show that it is possible to generate pure cultures of post-mitotic, human neurons from rapidly dividing NT2 teratocarcinoma cells following RA treatment. These non-dividing NT2-N cells have a stable neuronal phenotype and they can survive in culture for eight to ten weeks without the continuous presence of any exogenous differentiation promoting or trophic factors other than those in serum. Indeed, using the method of the invention, we have consistently produced NT2-N cells at weekly intervals for almost 2 years, and sufficient numbers of these cells were readily generated for biochemical experiments. It is also highly significant that the post-mitotic, neuron-like NT2-N cells continue to express proteins encoded by plasmids transfected into the undifferentiated NT2 cells. This combination of features is unique since, for the first time, cultured human cells with a fully differentiated neuronal phenotype are available in large numbers for the study of basic questions in neurobiology including timed neurite outgrowth, the basis and development of neurite polarity, cytoskeletal maturation and neuronal plasticity.

Besides the potential of NT2-N cells for studying the differentiated neuronal phenotype, NT2 cells are an important system for studying the mechanisms whereby RA can induce the differentiation of stem cells into committed neurons without the need for any other exogenous influences. Retinoids (especially RA) are known to have a teratogenic effect during embryogenesis, leading to neural crest and CNS defects. Additionally it has recently become clear that RA, and possibly other retinoids, have important in vivo physiologic roles in development outside of the nervous system. Studies of retinoid action during neuronal development have been hindered by the relative inaccessibility of the developing nervous system for experimentation. NT2 cells will provide a valuable in vitro system to study the cellular effects of retinoids and their role in neural induction and differentiation.

NT2-N cells expressed all of the key neuronal markers we examined. Further, they have specific characteristics which indicate that they are CNS (and not PNS) neurons (i.e., they express the 66 kD NF protein and do not express peripherin [Table I]). Like primary neurons in culture, NT2-N cells have a cytoskeleton dominated by the immature forms of MAPs and NF proteins (e.g., they express primarily fetal tau, MAP1b, MAP2b), but they do synthesize and maintain lower quantities of MAP 1a and NF-H. Given the stable neuronal phenotype assumed by NT2-N cells and the fact that they can be genetically engineered to express the products of transfected genes, these cells will be extremely useful for examining the cell biology and the functions of neuronal proteins in human neurons. The prompt neurite regeneration following replating (see FIG. 8) and the expression of well characterized cell adhesion molecules (see Table I) will allow NT2-N cells to be utilized for studying factors which regulate neurite outgrowth. Since NT2-N cells do not divide even in the presence of serum and they represent a reproducible source of highly purified human neuronal cultures, they may be useful cells for transplantation studies into nude mice and other mammals to determine their ability to integrate into the host environment. Indeed, the transfection of trophic factors or other proteins into NT2 cells that are then induced to differentiate into stable, post-mitotic neurons, may be useful as a novel delivery system for bioactive molecules in human neurodegenerative diseases.

The present invention provides methods for preparing a pure culture of post-mitotic human neurons comprising culturing undifferentiated human teratocarcinoma cells with retinoic acid to obtain a multi-layered culture; dispersing said cultured cells; and culturing said dispersed cells with a mitotic inhibitor or a combination of mitotic inhibitors. The present invention further contemplates that undifferentiated cells of the above method comprise NTera2/D1 cells. Moreover, the present invention includes this method wherein a combination of mitotic inhibitors comprises cytosine arabinoside, fluorodeoxyuridine and uridine. Additionally, dispersed cells of the above method can be cultured on Matrigel.

The present invention also provides methods for producing a stable population of post-mitotic human neurons expressing exogenous gene products comprising transfecting one or more plasmids (including a selectable marker) into cultured undifferentiated human teratocarctnoma cells; culturing said undifferentiated human teratocarcinoma cells with retinoic acid to obtain multi-layered culture; dispersing said cultured cells; and culturing said dispersed cells with a mitotic inhibitor or a combination of mitotic inhibitors. It is contemplated that a single selected expression vector may be transfected and expressed in the stable population of post-mitotic cells. It is further contemplated that more than one selected expression vector may be transfected and expressed in the stable population of post-mitotic cells. It is also contemplated that the selected expression plasmid comprises a β-galactosidase expression plasmid. The present invention contemplates that the undifferentiated cells of this transfection method comprise NTera2/D1 cells. It is further provided by the present invention that the combination of mitotic inhibitors of this transfection method comprise cytosine arabinoside, fluorodeoxyuridine and uridine. Additionally, the dispersed cells of this transfection method can be cultured on Matrigel.

The present invention also provides stable post-mitotic human neuron cells produced in accordance with the methods described above, including but not limited to stable post-mitotic human neuron cells substantially all of which comprise at least one transfected exogenous gens or stable post-mitotic human neuron cells which are not transfected.

The present invention is further illustrated by the following examples, which are not intended to be limiting in any way.

EXAMPLES

Example 1

Cell Culture

NT2 cells were maintained in DMEM HG including 10% fetal bovine serum and penicillin/streptomycin as previously described (Andrews, 1984). For differentiation, $2 \times 10^6$ cells were seeded in a 75cm$^2$ flask and treated with $1 \times 10^{-2}$ M RA (a $1 \times 10^{-2}$ M stock dissolved in DMSO was prepared fresh monthly) twice a week for four weeks. Following RA treatment, the cells were replated 1:6 (Replate #1; see FIG. 1). On the following two days, cells were mechanically dislodged, i.e., culture flasks were struck ten times on each side and the floating cells were washed with 5 ml of medium and replated again (Replate #2; see FIG. 1) on Matrigel (Collaborative Research) diluted 1:20 (for coverslips) or 1:60 (for dishes) following the manufacturer's instructions (the dilutions used for the Matrigel varied somewhat from lot to lot). Cells were seeded at a density of $0.2 \times 10^6$ cells per 12 mm coverslip or $7.5 \times 10^6$ cells per 100 mm dish in DMEM HG with 10% serum and penicillin/streptomycin supplemented with 1 µM Cytosine arabinoside, 10 µM fluorodeoxyuridine, and 10 µM uridine. Cytosine arabinoside was continued for the first week of culture and fluorodeoxyuridine and uridine for the first four weeks. For neurite regeneration experiments, three week old cultures were enzymatically removed with 0.025% dispase or 0.025% trypsin and replated (Replate #3; FIG. 1) on Matrigel, poly-D-lysine (10 µg/ml), or poly-D-lysine (10 µg/ml) plus laminin (10 µg/ml). Matrigel is a basement membrane extract containing collagen, laminin, and nidogen (Kleinman et al., 1986). This method as outlined in FIG. 1 and described in detail here, was applied to three different NTera2 subclones (NT2/D1, NT2/O3 and NT2/B9) with similar results. All results presented here were obtained from NT2/D1. During the course of the experiments it was observed that NT2 cells prefer Opti-MEM (GIBCO) with 5% fetal bovine serum (FBS) and this medium was then used for maintaining undifferentiated NT2 cells.

Example 2

BrDU labeling

Undifferentiated NT2 cells and differentiated NT2-N cells were grown free of mitotic inhibitors for four days and then labeled with 3 mg/ml BrDU for three hours (or up to 20 hours, in some cases). The cells were then washed, fixed and processed for indirect immunofluorescence as described below using BU-1, a mab which recognizes BrDU incorporated DNA without denaturation.

Example 3

Indirect immunofluorescence and Confocal Microscopy

Cells were washed with Hank's Buffered Salt Solution and fixed with 70% ethanol containing 0.15 M NaCl for ten minutes at room temperature. The cells were incubated with primary antibodies for one hour at room temperature, washed four times with PBS for one hour, incubated for one hour with secondary antibodies (donkey anti-mouse IgG coupled to rhodamine, donkey anti-rat coupled to fluorescein, and donkey anti-rabbit coupled to fluorescein; Jackson Immunoresearch), and finally washed four times in PBS for one hour before mounting in Aquamount (Lerner Labs). For confocal microscopy the procedure was essentially the same except that Texas Red conjugated secondary antibody was used instead of rhodamine and the coverslips were mounted using 5% DABCO to prevent bleaching. The coverslips were examined using a krypton laser on a Bio-Rad MRC-600 laser scanning confocal microscope.

Example 4

Peroxidase-Anti-Peroxidase (PAP) Immunocytochemistry

PAP immunocytochemistry was performed to visualize low levels of fetal tau because of the great sensitivity of this technique when compared to indirect immunofluorescence. The coverslips were fixed as above and blocked for 30 minutes with 0.1M Tris pH 7.0, including 2% calf serum and 0.25% cold water fish gelatin. Following this, the coverslips were processed as described previously in our laboratory for PAP immunocytochemistry (Carden et al., J. Neurosci., 7:3489–3504 (1987).

Example 5

Immunochemistry

MAP-enriched cytoskeletal samples were prepared by extracting the cells at room temperature for 15 minutes with 0.1 M MES pH6.8 containing 0.5 mM $MgSO_4$, 1 mM EGTA, 2 mM DTT, 2 mM GTP, 20 µM Taxol, 1% Triton X-100 and a cocktail of protease inhibitors. The pellets were recovered by centrifugation at 30,000 rpm in a TL100 ultracentrifuge for 30 minutes, solubilized in sample buffer without dye and the protein concentrations of the samples were determined using a Coomassie blue dye binding assay (Pierce). These samples were run on SDS-PAGE gels and then electroblotted to nitrocellulose membranes for probing with antibodies using methods described previously in our laboratory (Lee et al., 1987).

Example 6

$^3$H-Uridine Labelling of NT2-N Cells 60 mm dishes of NT2-N cells were incubated with 50 µCi of [5,6-$^3$H]uridine (1.70 Tbq/mmol) for 16–24 hours. These dishes were then washed with PBS containing 10 µM unlabelled uridine and fixed with Bouin's fixative. The dishes were then coated with NTB-2 emulsion diluted 1:1 with water, dried overnight and stored at 4°C. for four days. The dishes were developed for one minute in Kodak D19 and fixed with Kodak Rapid-Fix.

Example 7

Transfection and Staining for β-galactosidase

Undifferentiated NT2 cells were transfected with 100 µg SPUD1 and 10 µg of pSV2neo by lipofection using Lipofectln (Bethesda Research Laboratories). After two days in complete medium, the transfectants were selected with 200 µg/ml G418 (Gibco) for seven days. Cells were stained for β-galactosidase activity with 1 mg/ml X-gal, 5 mM potassium ferrocyanide, 5 mM potassium ferricyanide, 2 mM $MgCl_2$ in PBS after fixation in 2% paraformaldehyde, 0.2% glutaraldehyde in phosphate buffered saline pH7.4. β-gal positive cultures were subcloned twice and the subclones were used for further studies. SPUD1 (kindly provided by Dr. C. Cepko) is a β-galactosidase expression vector which utilizes the SV40 promoter and has Moloney murine leukemia virus long terminal repeats upstream and downstream. The cells were photographed using Hoffman modulation contrast to allow the simultaneous visualization of the blue reaction product and the processes.

What is claimed:

1. An at least 95% pure homogeneous culture of stable post-mitotic human neuron cells substantially all of which comprise at least one transfected gene wherein said cells are produced by culturing NT2 cells with retinoic acid.

2. The pure, homogenous culture of stable post-mitotic human neuron cells of claim 1 wherein said culture is at least 99% pure.

3. The pure, homogenous culture of stable post-mitotic human neuron cells of claim 1 wherein said culture comprises at least $10 \times 10^6$ neurons.

4. The pure, hoomogenous culture of stable post-mitotic human neuron cells of claim 1 wherein said culture is at least 99% pure and comprises at least $10 \times 10^6$ neurons.

5. An at least 95% pure homogeneous culture of stable post-mitotic human neuron cells produced by culturing NT2 cells with retinoic acid.

6. The pure, homogenous culture of stable post-mitotic human neuron cells of claim 5 wherein said culture is at least 99% pure.

7. The pure, homogenous culture of stable post-mitotic human neuron cells of claim 5 wherein said culture comprises at least $10 \times 10^6$ neurons.

8. The pure, homogenous culture of stable post-mitotic human neuron cells of claim 5 wherein said culture is at least 99% pure and comprises at least $10 \times 10^6$ neurons.

* * * * *

UNITED STATES PATENT AND TRADEMARK OFFICE
CERTIFICATE OF CORRECTION

PATENT NO. : 5,654,189

DATED : Aug. 5, 1997

INVENTOR(S) : Lee et al.

It is certified that error appears in the above-indentified patent and that said Letters Patent is hereby corrected as shown below:

At col 1, line 30, please delete "gens" and insert therefor --gene--.

At col 13, line 39, please delete "Lipofectln" and insert therefor --Lipofectin--.

At col 14, line 25, please delete "hoomogenous" and insert therefor --homogenous--.

Signed and Sealed this

Twenty-second Day of September, 1998

Attest:

BRUCE LEHMAN

Attesting Officer

Commissioner of Patents and Trademarks